United States Patent [19]

Moon

[11] 4,153,707
[45] May 8, 1979

[54] FUNGICIDAL ISOXAZOLYL PHENOLS AND METHOD OF USE

[75] Inventor: Malcolm W. Moon, Kalamazoo, Mich.

[73] Assignee: The Upjohn Company, Kalamazoo, Mich.

[21] Appl. No.: 850,213

[22] Filed: Nov. 10, 1977

Related U.S. Application Data

[63] Continuation-in-part of Ser. No. 713,922, Aug. 12, 1976, Pat. No. 4,065,574, which is a continuation-in-part of Ser. No. 608,850, Aug. 29, 1975, abandoned, which is a continuation of Ser. No. 457,056, Apr. 1, 1974, abandoned.

[51] Int. Cl.² .................... A61K 31/42; C07D 261/08
[52] U.S. Cl. ............................... 424/272; 260/307 H
[58] Field of Search ..................... 260/307 H; 424/272

[56] References Cited

U.S. PATENT DOCUMENTS

| | | | |
|---|---|---|---|
| 3,752,819 | 8/1973 | Philippe | 260/307 H |
| 4,065,574 | 12/1977 | Moon et al. | 424/283 |
| 4,072,689 | 2/1978 | Tarzia | 424/272 |

FOREIGN PATENT DOCUMENTS

| | | |
|---|---|---|
| 2513652 | 10/1975 | Fed. Rep. of Germany. |
| 1025697 | 4/1966 | United Kingdom ................ 260/307 H |

Primary Examiner—Donald G. Daus
Assistant Examiner—David E. Wheeler
Attorney, Agent, or Firm—John J. Killinger; Roman Saliwanchik

[57] ABSTRACT

A compound of the formula:

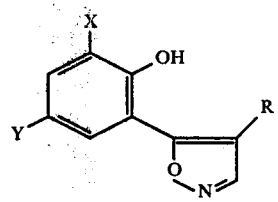

wherein X is a member selected from the group consisting of hydrogen, alkyl of from 1 to 3 carbon atoms, inclusive, chlorine or bromine; Y is a member selected from the group consisting of hydrogen, chlorine or bromine and R is a member selected from the group consisting of hydrogen or lower alkyl of from 1 to 3 carbon atoms.

The compounds can be applied to seeds, plants, animals, objects, or places for preventing damage due to fungi. General methods for preparing the active compounds, compositions and methods of use are shown.

30 Claims, No Drawings

FUNGICIDAL ISOXAZOLYL PHENOLS AND METHOD OF USE

CROSS REFERENCE TO RELATED APPLICATIONS

This application is a continuation-in-part of application Ser. No. 713,922, filed Aug. 12, 1976, now allowed as U.S. Pat. No. 4,065,574, which is a continuation-in-part of application Ser. No. 608,850, filed Aug. 29, 1975, now abandoned, which in turn is a continuation of application Ser. No. 457,056, filed Apr. 1, 1974, now abandoned.

In the parent applications the structure of the active compounds were erroneously described as 4-chromone oximes. It has since been found that the compounds are isoxazoles of the Formula I.

SUMMARY OF THE INVENTION

A compound of the formula:

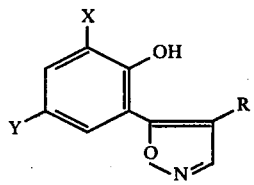

Formula I wherein X is a member selected from the group consisting of hydrogen, alkyl of from 1 to 3 carbon atoms, inclusive, chlorine or bromine; Y is a member selected from the group consisting of hydrogen, chlorine or bromine and R is a member selected from the group consisting of hydrogen or lower alkyl of from 1 to 3 carbon atoms.

The compounds are compounded in association with agricultural carriers for application to substrates where fungal growth is found.

DETAILED DESCRIPTION OF THE INVENTION

The compounds of the Formula I are prepared from 4-chromone compounds of the formula:

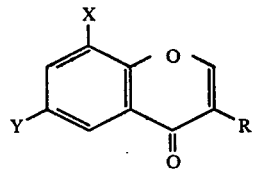

Formula II wherein X is a member selected from the group consisting of hydrogen, alkyl of from 1 to 3 carbon atoms, inclusive, including isomeric forms thereof, e.g., methyl, ethyl, propyl and isopropyl, chlorine or bromine.

Y is a member selected from the group consisting of hydrogen, chlorine or bromine and R is a member selected from the group consisting of hydrogen or lower alkyl of from 1 to 3 carbon atoms, inclusive, including isomeric forms thereof, e.g., methyl, ethyl, propyl or isopropyl.

The starting 4-chromones of the Formula II are readily synthesized according to methods described by Wawzonek, S. in Chapter 8 entitled "Chromones, Flavones, and Isoflavones" of Elderfield's *Heterocyclic Compounds*, Vol. 2, pp. 229–276 (1951), John Wiley and Sons, Inc., N.Y.

The 4-chromones of the Formula II are readily converted to the isoxazoles of the Formula I with hydroxylamine hydrochloride in a suitable solvent, e.g., ethanol, methanol and isopropanol with heating under reflux.

The following examples are illustrative of the process and products of the present invention but are not to be construed as limiting.

EXAMPLE 1

Preparation of 2,4-dichloro-6-(4-methyl-5-isoxazolyl)phenol

Part A - 3,5-Dichloro-2-hydroxypropiophenone

A mixture consisting of 1467.09 g. (9.0 moles) 2,4-dichlorophenol and 832.77 g. (9.0 moles, 783 ml.) propionyl chloride was thoroughly mixed by stirring at 25° C. for 18 hours. After introducing gaseous nitrogen into the reaction vessel in order to eliminate any oxygen present, 1500.3 g. (11.25 moles) aluminum chloride was added slowly, and the reaction mixture was slowly heated to 150° C. with stirring. Heating and stirring were continued for 3 hours. The reacted mixture was then cooled to 100° C., and a mixture consisting of 2250 ml. water and 2250 ml. concentrated hydrochloric acid was added slowly. An additional 2250 ml. water was added, before the acidified reaction mixture was poured onto 8 l. crushed ice. A precipitate formed which was collected on a filter and washed thoroughly with water. The washed filter cake was recrystallized from 5500 ml. acetone to give 1810.4 g. (91.8% yield) of 3,5-dichloro-2-hydroxypropiophenone as tan needles having a melting point at 117° to 119° C.

Part B—6,8-Dichloro-3-methyl-4-chromone

A 876 g. portion (4.0 moles) of the 3,5-dichloro-2-hydroxypropiophenone prepared in Part A, above, was mixed in a 22 l. reaction vessel with 2820 ml. methyl formate and 4000 ml. dimethyl ether ethylene glycol (Glyme). The vessel was fitted with a reflux condenser, a mechanical stirrer, and an addition funnel. To the mixture was slowly added with vigorous stirring over an interval of 30 min. 540 g. (10 moles) of sodium methoxide. There was vigorous foaming, and the temperature of the reaction mixture increased to about 45° C. There was a change from brown to yellow color. Stirring was continued for 30 min. At this point, 3000 ml. concentrated hydrochloric acid is added as rapidly as possible with continuous stirring and caution. The temperature increased to 55° C. and a heavy precipitate formed. Stirring was continued for one hour, before collecting the precipitate on a filter. The filter cake was washed thoroughly with water, and after drying 884 g. (96.6% yield) 6,8-dichloro-3-methylchromone was obtained that had a melting point at 141° to 142° C.

Part C—2,4-Dichloro-6-(4-methyl-5-isoxazolyl)phenol

A quantity (652 g., 2.85 moles) of the 6,8-dichloro-3-methyl-4-chromone prepared in Part B, above, was gently heated and dissolved in 14 l. ethanol. The reaction vessel was fitted with two reflux condensers and heated over a steam bath. There was added 792.3 g. (11.4 moles) hydroxylamine hydrochloride, and heating at the reflux temperature was continued for 48 hours. The ethanol solvent was then removed by distillation until a precipitate began to form (about 5 l. were distilled). Six liters of water were added and crystals formed. The crystals were collected on a filter and washed with 4 l. water. The combined wash water and filtrate was chilled in a refrigerator and a second crop of crystals were recovered. There are thus obtained 667.8 g. (96.2% yield) of 2,4-dichloro-6-(4-methyl-5-isoxazolyl)phenol which was grey solid having a melting point at 159° to 160° C.

EXAMPLE 2

2-chloro-6-(4-methyl-5-isoxazolyl)phenol

Part A—2-Chlorophenyl propionate

To 205.0 g. (1.60 moles) of o-chlorophenol was added 150 ml. (1.73 moles) of propionyl chloride dropwise during 1.5 hour. The solution was then slowly heated to 100° C., allowed to cool to 80° C., placed under vacuum and allowed to cool to room temperature overnight to yield 297.2 g. of 2-chlorophenyl propionate.

Part B—3-Chloro-2-hydroxypropiophenone

To 36.9 g. (0.200 mole) of 2-chlorophenylpropionate cooled in an ice bath was added 50 ml. of titanium tetrachloride and the mixture was heated at 90° C. for 17 hours. Then 100 ml. of 3 N hydrochloric acid was added and the suspension was steam distilled to yield 9.90 g. (26.8%) of 3-chloro-2-hydroxypropiophenone.

Part C—8-Chloro-3-methyl-4-chromone

To 15.85 g. (0.0856 moles) of 3-chloro-2-hydroxypropiophenone was added 61 ml. of methyl formate and 87 ml. of glyme then 11.7 g. (0.217 mole) of sodium methoxide. The suspension was stirred for 0.5 hour, then 75 ml. of concentrated hydrochloric acid was added, the solution was stirred for 1.5 hour and filtered. The solids were taken up in benzene, dried over sodium sulfate, and the solvent was removed to yield 6.85 g. of crude product, which was chromatographed on 350 g. of silica gel with benzene-ethyl acetate to yield 5.20 g. (31.1%) of 8-chloro-3-methyl-4-chromone.

Part D—2-Chloro-6-(4-methyl-5-isoxazolyl)phenol

To 4.87 g. (0.25 mole) of 8-chloro-3-methyl-4-chromone in 50 ml. of 95% ethanol was added 6.95 g. (0.1 moles) of hydroxylamine hydrochloride and the solution was refluxed for 117 hours. The solvent was removed under vacuum, the residue was diluted with water, the solids were filtered, dried, and recrystallized twice from benzene to yield 3.35 g. (63.9%) of 2-chloro-6-(4-methyl-5-isoxazolyl)phenol, m.p. 136.8° C.

Analysis: Calc'd. for $C_{10}H_8ClNO_2$: C, 57.30; H, 3.85; N, 6.68. Found: C, 57.15; H, 3.85; N, 6.75.

EXAMPLE 3

Following the procedure of the preceding example 1, Part C, but substituting an equimolar amount of
  6,8-dichloro-3-ethyl-4-chromone,
  6,8-dibromo-3-methyl-4-chromone,
  3-methyl-4-chromone,
  3,6-dimethyl-4-chromone,
  3-methyl-6-chloro-4-chromone,
  6,8-dichloro-4-chromone,
  6-chloro-4-chromone,
  3-propyl-4-chromone for the 6,8-dichloro-3-methyl-4-chromone of the example there is obtained
  2,4-dichloro-6-(4-ethyl-5-isoxazolyl)phenol,
  2,4-dibromo-6-(4-methyl-5-isoxazolyl)phenol,
  2-(4-methyl-5-isoxazolyl)phenol,
  4-methyl-2-(4-methyl-5-isoxazolyl)phenol,
  4-chloro-2-(4-methyl-5-isoxazolyl)phenol,
  2,4-dichloro-6-(5-isoxazolyl)phenol,
  4-chloro-2-(5-isoxazolyl)phenol, and
  2-(4-propyl-5-isoxazolyl)phenol, respectively.

A principal objective of this invention is to provide a new method for killing and controlling fungi whenever the microorganisms are found. The method of the invention is not limited as to locale of the target fungi; and the new method is applicable to various situs, objects of all types, animals, and plants. The new method is broadly accomplished by contacting the fungi with the newly recognized antifungal compounds of the Formula I wherever undesired fungi are causing a problem.

A further main objective of the invention is to provide new formulations for killing and controlling fungi. The preferred kind of formulations are dispersible ones that lend themselves to even distribution over areas where an undesired fungus is infective or potentially infective. In this general embodiment of the invention liquid dispersible carriers are frequently used, but solid pulverulent carriers are sometimes preferred. Ofttimes, adjuvants such as surface active agents, dispersants, and adhesive or sticking agents are included.

The novel formulations of the invention are used to kill and control fungi on organic matter such as wood, cellulosic fibers, leather, seeds, fruits, vegetables, living plants, and on various animals, for example, fishes, reptiles, birds, cattle, horses, dogs, and cats. When an undesired fungus is causing a problem, one merely contacts the microorganism with an effective amount of one or more active compounds of the invention and utilizing one of the conventional techniques known to those skilled in the art.

Living plants have been protected in accordance with the new method of this invention by spraying a solution of the compounds on the plants themselves or on the soil proximate to where the plants are growing and within reach of the root systems. The active compounds are apparently absorbed by the root hairs and systemically transported throughout the plant so as to prevent damage by fungal pathogens.

The compounds of Formula I can be used as antifungal agents in pure form, as technical grade chemicals, as crude preparations, or as formulations with solid and liquid carriers with or without adjuvants. In general, the interest of practical modes of applications and economies are best served by the formulations of the invention. The pure active compounds (including mixtures thereof) or the formulations can be applied to fungi, objects, or a situs for preventing fungal growth and propagation. The antifungal formulation of this invention include dispersions in powder and granular carriers, e.g, dusts and granules; dispersions in liquid carriers, e.g., true solutions, suspensions and emulsifiable concentrate; smokes and aerosols; emulsions, e.g., creams and ointments; and capsules and tablets.

Most of the compounds according to Formula I are solids are commonly experienced temperatures and they can be readily formulated as dusts by grinding a mixture of the compound and a pulverulent carrier in the presence of each other. Grinding is conveniently accomplished in a ball mill, a hammer mill, or by airblast micronization. A suitable ultimate particle size is less than 60 microns. Preferably, 95% of the particles are less than 50 microns, and about 75% are 5 to 20 microns. Dusts of that degree of comminution are conveniently free-flowing and can be applied to animals, inanimate matter, fruit trees, crop plants, and soil so as to effect thorough distribution and coverage. Dusts are particularly adapted for effectively controlling plant fungi over wide areas when applied by airplane. They are also indicated for application to the undersides of plant foliage and to the skin of hairy animals.

Representative suitable pulverulent carriers include the natural clays such as China, Georgia, Barden, attapulgus, kaolin, and bentonite clays; minerals in their natural forms as they are obtained from the earth such as talc, pyrophyllite, quartz, diatomaceous earth, fuller's earth, chalk, rock phosphates and sulfates, calcium carbonates, sulfur, silica and silicates; chemically modified minerals such as washed bentonite, precipitated calcium phosphate, precipitated calcium carbonate, precipitated calcium silicate, synthetic magnesium silicate, and colloidal silica; and organic flours such as wood, walnut shell, soybean, cottonseed, and tobacco flours, and free-flowing, hydrophobic starches.

Dusts can also be prepared by dissolving the active compounds in a volatile solvent such as methylene chloride, mixing the solution with a pulverulent carrier and evaporating the solvent before grinding to particulate dimensions.

The proportions of pulverulent carrier and active compound can vary over a wide range depending upon the fungi to be killed or controlled and the conditions of treatment. In general, dust formulations can contain up to about 90% (on a weight basis) of the active ingredient. Dusts having as little as 0.001% of the active ingredient can be used, but a generally preferred proportion is from about 0.50% to about 20% of active ingredient.

The dispersible powder formulations of this invention are prepared by incorporating a surface active agent in a dust composition prepared as described above. When about 0.1% to about 12% of such agent is incorporated in a dust, the dispersible powder thus obtained is particularly adapted for further admixture with water for spraying on inanimate matter and products, fruit trees, field crops, soil, and livestock. The dispersible powders can be admixed with water to obtain any desired concentration of active ingredient, and the mixture can be applied in amounts sufficient to obtain predetermined rates of application and uniform distribution. With this flexibility of mind, the dispersible powders of the invention can conveniently comprise preferably about 10% to about 80% of active ingredient.

Representative surface active agents useful for preparing dispersible powder formulations of this invention include alkyl sulfates and sulfonates, alkyl aryl sulfonates, sulfosuccinate esters, polyoxyethylene sulfates, polyoxyethylene-sorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. The preferred class of surfactants includes blends of sulfonated oils and polyalcohol carboxylic acid esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, and X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul N4S). It will be understood, of course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1% or less. The dispersible powder compositions can be formulated with a mixture of surfactants of the types indicated if desired.

A suitable dispersible powder formulation is btained by blending and milling 327 lbs. of Georgia Clay, 5.0 lbs. of isooctylphenoxy polyethoxy ethanol (Triton X-100) as a wetting agent, 10 lbs. of a polymerized sodium salt of substituted benzoid long-chain sulfonic acid (Daxad 27) as a dispersing agent, and 340 lbs. of the active ingredient. The resulting formulation has the following percentage composition (parts herein are by weight unless otherwise specified):

| | |
|---|---|
| Active ingredient | 50.00% |
| Isooctylphenoxy polyethoxy ethanol | 0.75% |
| Polymerized sodium salt of substituted benzoid long-chain sulfonic acid | 1.25% |
| Georgia Clay | 48.00% |

This formulation, when dispersed in water at the rate of 10 lbs. per 100 gals., gives a spray formulation containing about 0.6% (6000 ppm) active ingredient which can be applied to fungus infected soil, plants, or turf at the rate of 40 gals. per acre to give a total application of active ingredient of 2 lbs. per acre.

If desired, dispersants such as methyl cellulose, polyvinyl alcohol, sodium ligninsulfonates, and the like can be included in the dispersible powder formulations of this invention. Adhesive or sticking agents such as vegetable oils, naturally occurring gums, casein, and others can also be included. Corrosion inhibitors such as epichlorohydrin and antifoaming agents such as stearic acid can also be included.

The granular formulations according to this invention are prepared by permeating a granular carrier with a solution of a compound according to Formula I and then drying the granules. Suitable granular carriers include vermiculite, expanded vermiculite, pyrophyllite, and attapulgite. Suitable solvents include acetone, methylethyl ketone and methylene chloride. A solution of, for example, 3-ethyl-4-chromanone oxime is sprayed on a granular carrier while the carrier is being mixed and tumbled. The granules are then dried. The granules can range in size from about 10 to about 60 mesh, preferably about 30 to 60 mesh.

The antifungal compounds of this invention can be applied to fungi, objects, or a situs in aqueous sprays without a solid carrier. Since, however, many of the compounds themselves are relatively insoluble in water, such compounds are preferably dissolved in a suitable inert organic solvent carrier. Advantageously, the solvent carrier is immiscible with water so that an emulsion of the solvent carrier in water can be prepared. If, for example, a water-miscible solvent carrier such as ethanol is used the solvent carrier will dissolve in the water and any excess compound will be thrown out of solution. In an oil-in-water emulsion, the solvent phase is dispersed in the water phase and the dispersed phase contains the active ingredient. In this way, uniform distribution of a water insoluble active ingredient is achieved in an aqueous spray. A solvent carrier in which the compounds are highly soluble is desirable so that relatively high concentrations of active ingredient can be obtained. Sometimes, one or more solvent carriers with or without a cosolvent can be used in order to obtain concentrated solutions of the active ingredient, the main consideration being to employ a waterimmiscible solvent for the active ingredient that will hold the compound in solution over the range of concentrations useful for preventing fungal growth and propagation.

The emulsifiable concentrates of the invention are prepared, therefore, by dissolving the active ingredient and a surfactant in a substantially water-immiscible solvent carrier (i.e., a solvent carrier which is soluble in water to the extent of less than 2.5% by volume at temperatures of the order of 20° to 30° C.), for example, cyclohexanone, methyl propyl ketone, summer oils, ethylene dichloride, aromatic hydrocarbons such as benzene, toluene, and xylene, and high-boiling petroleum hydrocarbons such as kerosene, diesel oil, and the like. If desired, a cosolvent such as methyl ethyl ketone, acetone, isopropanol, and the like can be included with the solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed, if desired.

Advantageously, the concentration of active ingredient in the emulsifiable concentrates can range from about 5% to about 50% by weight, preferably from about 10% to about 40%. A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1 qt. of a 20% concentrate mixed with 40 gals. of water provides about 1200 ppm (parts per million) of active ingredient. In the same manner, more concentrated solutions of active ingredient can be prepared.

The concentrate formulations of the invention which are intended for use in the form of aqueous dispersions or emulsions can also comprise a humectant, that is to say, an agent which will delay the drying of the composition in contact with material to which it has been applied. Suitable humectants include glycerol, diethylene glycol, solubilized lignins, such as calcium ligninsulfonate, and the like.

The rates of application to fungi, objects or situs will depend upon the species of fungi to be controlled, the presence or absence of desirable living organisms, temperature conditions of treatment, and the method and efficiency of application. In general, fungicidal activity is obtained when the compounds are applied at concentrations of about 10 to about 6,000 ppm, preferably at concentrations of about 100 to about 1,200 ppm.

The composition containing compounds according to the invention, can be applied by conventional methods to fungi, objects or any situs where control of fungi is desired. For example, an area of soil or plants can be treated by spraying wettable powder suspensions, emulsions or solutions from boom-type power sprayers or from hand-operated knapsack sprayers. Dusts can be applied by power dusters, or by hand-operated dusters. Creams and ointment formulations can be applied to skin or objects for prolonged protection against the fungi.

The following examples are illustrative of the method and formlations of the invention but are not to be construed as limiting.

EXAMPLE 4

A field test with a representative compound and formulation embodiment of this invention was accomplished by treating seeds with the compound, planting them, and noting the incidence of damping-off among the protected seedlings as compared with seedlings from untreated seeds.

The compound was 2,4-dichloro-6-(4-methyl-5-isoxazolyl)-phenol and it was utilized in a wettable powder formulation consisting of 50% the compound, 3% sodium alkyl naphthalene sulfonate (Nekal BA-77), 8% sodium lignosulfonate (polyfon H), and Barden Clay (39%). The air milled formulation was dry coated on the seeds. The several kinds of seeds used were Garden Peas (variety, Little Marvel), Sugar Beets (variety, Type E), Red Sorghum (variety unknown), White Sorghum (variety unknown), Oates (variety unknown), Wheat (variety unknown), Lima Beans (variety, Henderson's Bush), and Cotton (variety, Delta Pine 16).

The amount of compound per hundredweight of seeds varied from crop to crop as is shown in the Table, but ranged in general from about 1 ox. to about 6 ozs.

The test seeds were planted in soil, plotted into areas comprising 5 single replicate rows, the rows being 17 feet long, 36 inches apart. One hundred seeds were planted per row. The soil had been prepared by plowing down a urea fertilizer (45% nitrogen) at the rate of 300 lbs. per acre during the first week in May. The following week, a complete fertilizer 6-24-24 was broadcast over the plots at the rate of 300 lbs. per acre. The red and white sorghums were planted May 14. The wheat and oats were planted May 15. The sugar beets, lima beans, and peas were planted May 16. And the cotton was not planted until June 8.

No irrigation water was applied, because rainfall was adequate as shown by the following records.

| Date | Rainfall in inches | Date | Rainfall in inches |
| --- | --- | --- | --- |
| 5/20/73 | 0.30 | 6/5/73 | 0.18 |
| 5/22/73 | 0.60 | 6/17/73 | 0.06 |
| 5/23/73 | 0.53 | 6/20/73 | 0.43 |
| 5/26/73 | 1.16 | 6/23/73 | 0.68 |
| 5/28/73 | 0.80 | 6/27/73 | 1.39 |
| 5/29/73 | 0.25 | 6/28/73 | 0.28 |
| 5/30/73 | 0.59 | 6/30/73 | 0.06 |
| 5/31/73 | 0.04 | 7/2/73 | 0.82 |
| 6/3/73 | 0.75 | 7/4/73 | 0.20 |
| 6/4/73 | 0.12 | | |

After 4 to 5 weeks had passed, and germination and relative vigor of seedlings could be observed, the stand of each replicate of each crop was evaluated. Some of the obviously diseases plants, and soil samples from root zones were assayed for the predominant disease organisms. The results were as follows:

| Crop | Oz. Active/Cwt. | Date Determined | Average % Germination |
| --- | --- | --- | --- |
| Cotton | 2.0 | July 6 | 71.0 |
| | 4.0 | | 70.2 |
| | 6.0 | | 77.2 |
| | none | | 57.4 |
| Lima Beans | 1.0 | June 26 | 48.0 |
| | 3.0 | | 47.6 |
| | none | | 10.8 |

| Crop | Oz. Active/Cwt. | Date Determined | Average % Germination |
|---|---|---|---|
| Oats | 2.0 | June 21 | 61.8 |
|  | 4.0 |  | 67.0 |
|  | none |  | 51.2 |
| Peas | 1.0 | June 21 | 76.4 |
|  | 2.0 |  | 74.0 |
|  | none |  | 52.8 |
| Red Sorghum | 1.0 | June 20 | 60.2 |
|  | 2.5 |  | 55.2 |
|  | none |  | 26.0 |
| Sugar Beets | 3.0 | June 20 | 64.6 |
|  | 6.0 |  | 60.2 |
|  | none |  | 32.0 |
| Wheat | 1.0 | June 21 | 55.6 |
|  | 3.0 |  | 54.8 |
|  | none |  | 46.6 |
| White Sorghum | 1.0 | June 20 | 72.0 |
|  | 2.5 |  | 69.2 |
|  | none |  | 30.0 |

The disease organisms Pythium, Fusarium, and possibly Phytophthora were isolated from the samples of soil and from diseased plants. The target microorganisms include the foregoing ones as well as Rhizoctonia.

The foregoing tabulated data show that a representative, preferred compound of this invention was especially effective in preventing damage to seedlings and enhancing the stand of plants. These results are comparable to or better than those obtained with accepted commercial fungicides in the same test.

Applicants accordingly contemplate a reasonably similar degree of effectiveness with the compounds of this invention as described by the general Formula I and by the specific compounds named when a susceptible fungus is involved, and an effective antifungal amount of compound is used.

In accordance with their further contemplation other crops will be similarly benefited by treatment with the new fungicides of this invention at rates of 0.5 oz. to 20.0 ozs. per hundredweight preferably 1 oz. to 6 ozs. per hundredweight. Representative control of Rhizoctonia damage is effected by dispersing a 50% wettable powder of a isoxazole according to Formula I in water and applying the formulation to soil. The wettable powder comprises a finely divided clay and one or more surface active agents besides the active ingredient. By appropriately dispersing an amount of the wettable powder in water, test concentrations of the active ingredient are obtained, e.g., 9.6 mg. per ml., 4.8 mg. per ml., 2.4 mg. per ml. and so forth. A volume of the aqueous dispersion is used, e.g., 25 ml. on the soil in a 5" clay pot that will provide a desired per acre rate of application, e.g., 1, 2½, 5, 10, 20, or more lbs. per acre. The plants protected in the tests are susceptible ones such as beans, peas, cotton, squash, cucumbers, and pumpkins. The test plants are observed for example at 7, 9, 11, 14, and 21 days after application. The compounds of this invention prevent Rhizoctonia damage to the young plants and therefore they grow more vigorously and are more productive.

EXAMPLE 5

A wettable powder concentrate having the following percentage composition:

| | |
|---|---|
| 2,4-dichloro-6-(4-methyl-5-isoxazolyl)phenol | 50% |
| Sodium alkyl naphthalene sulfonate (Nekal BA-77) | 3% |
| Polyfon H | 8% |
| Barden Clay | 39% | was prepared by mixing 300 gm. of the isoxazole, 18 gm. of a sodium alkyl naphthalene sulfonate (Nekal BA-77), 48 gm. of polyfon H, and 234 gm. of Barden Clay. The mixture was airmilled to a particle size averaging 5 to 30 microns. It was suspended in 10 gals. of water, giving an aqueous spray containing about 7000 parts per million of active ingredient.

EXAMPLE 6

A fine granular formulation having the following percentage composition:

| | |
|---|---|
| 2,4-dichloro-6-(4-methyl-5-isoxazolyl)phenol | 3.7% |
| Expanded vermiculite (30/60 mesh) | 96.3% | was prepared by spraying a solution of 220 gm. of the isoxazole in 1000 ml. of methylene chloride on 5780 gm. of expanded vermiculite (30 to 60 mesh) while the vermiculite was being tumbled and stirred so as to assure even distribution. The methylene chloride was then evaporated, leaving the isoxazole adsorbed on the vermiculite particles, and the vermiculite was pulverized.

EXAMPLE 7

An emulsifiable concentrate having the following percentage composition:

| | |
|---|---|
| 2,4-dichloro-6-(4-methyl-5-isoxazolyl)phenol | 15.0% |
| Technical alkyl naphthaline boiling at 238° to 293° C. (Velsicol AR$_{50}$) | 19.7% |
| Xylene | 17.4% |
| Isopropanol | 17.4% |
| Ethylene dichloride | 25.4% |
| Blend of alkyl aryl sulfonates and alkylphenoxy polyethoxy ethanols (Triton X-151) | 5.1% | was prepared by mixing 15.0 lbs. of the isoxazole, 19.7 lbs. of Velsicol AR$_{50}$, 17.4 lbs. of zylene, 17.4 lbs. of isopropanol, 25.4 lbs. of ethylene dichloride, and 5.1 lbs. of Triton X-151.

6.67 Lbs. of the concentrate mixed with 10 gal. of water gave a spray emulsion containing 11,000 ppm of isoxazole.

EXAMPLE 8

An emulsifiable concentrate having the following percentage composition:

| | |
|---|---|
| 2,4-dichloro-6-(4-methyl-5-isoxazolyl)phenol | 40.0% |
| Technical alkyl naphthalene boiling at 238° to 293° C. (Velsicol AR$_{50}$) | 13.7% |
| Xylene | 12.3% |
| Isopropanol | 11.3% |
| Ethylene dichloride | 17.7% |
| Blend of alkyl aryl sulfonates and alkylphenoxy polyethoxy ethanols (Triton X-151) | 5.0% | was prepared by mixing 40.0 lbs. of isoxazole, 13.7 lbs. of Velsicol AR$_{50}$, 12.3 lbs. of xylene, 11.3 lbs. of isopropanol, 17.7 lbs. of ethylene dichloride, and 5.0 lbs. of Triton X-151.

1.67 Lbs. of the concentrate mixed with 10 gals. of water gave a spray emulsion containing 8,000 ppm of isoxazole for control of fungi.

EXAMPLE 9

A wettable powder concentrate having the following percentage composition:

| | |
|---|---|
| 2,4-dichloro-6-(4-methyl-5-isoxazolyl)phenol | 50% |
| Kaolinite Clay (finely divided) | 46% |
| Sodium salt of condensed mono-naphthalene sulfonic Acid (Lomar D) | 4% | was prepared by mixing 50 g. of isoxazole, 46 g. of the kaolinite clay, and 4 g. of Lomar D. The mixture was milled to an average particle size of 5 to 30 microns.

EXAMPLE 10

A granular formulation having the following percentage composition:

| | |
|---|---|
| 2,4-dichloro-6-(4-methyl-5-isoxazolyl)phenol | 1% |
| Pyrophyllite (30/60 mesh) | 99% | was prepared by dissolving 1.0 lb of isoxazole in 10.0 l. of ethylene dichloride and spraying the solution on 99.0 lbs. of pyrophyllite. The granules were dried and then packaged for use.

EXAMPLE 11

Following the procedure of the preceding Examples 5 through 10, inclusive, substituting an equimolar amount of the compounds prepared in Examples 2 and 3, there are obtained compositions useful for controlling undesired fungal growth.

I claim:
1. A compound of the formula:

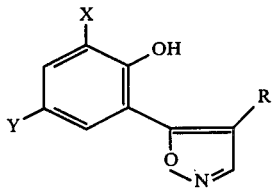

wherein X is a member selected from the group consisting of hydrogen, alkyl of from 1 to 3 carbon atoms, inclusive, chlorine or bromine; Y is a member selected from the group consisting of hydrogen, chlorine or bromine and R is a member selected from the group consisting of hydrogen or lower alkyl of from 1 to 3 carbon atoms, inclusive.

2. A compound according to claim 1 which is 2,4-dichloro-6-(4-methyl-5-isoxazolyl)phenol.

3. A compound according to claim 1 which is 2,4-dichloro-6-(4-ethyl-5-isoxazolyl)phenol.

4. A compound according to claim 1 which is 2,4-dibromo-6-(4-methyl-5-isoxazolyl)phenol.

5. A compound according to claim 1 which is 2-chloro-6-(4-methyl-5-isoxazolyl)phenol.

6. A compound according to claim 1 which is 2-(4-methyl-5-isoxazolyl)phenol.

7. A compound according to claim 1 which is 4-methyl-2-(4-methyl-5-isoxazolyl)phenol.

8. A compound according to claim 1 which is 4-chloro-2-(4-methyl-5-isoxazolyl)phenol.

9. A compound according to claim 1 which is 2,4-dichloro-6-(5-isoxazolyl)phenol.

10. A compound according to claim 1 which is 4-chloro-2-(5-isoxazolyl)phenol.

11. A method for controlling fungi comprising the application of an effective antifungal amount of a compound of the formula:

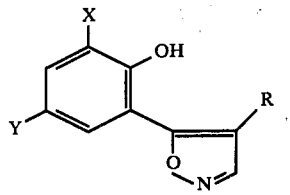

wherein X is a member selected from the group consisting of hydrogen, alkyl of from 1 to 3 carbon atoms, inclusive, chlorine or bromine; Y is a member selected from the group consisting of hydrogen, chlorine or bromine and R is a member selected from the group consisting of hydrogen or lower alkyl of from 1 to 3 carbon atoms, inclusive, to fungi, objects or a situs.

12. A method according to claim 11 which is 2,4-dichloro-6-(4-methyl-5-isoxazolyl)phenol.

13. A method according to claim 11 which is 2,4-dichloro-6-(4-ethyl-5-isoxazolyl)phenol.

14. A method according to claim 11 which is 2,4-dibromo-6-(4-methyl-5-isoxazolyl)phenol.

15. A method according to claim 11 which is 2-chloro-6-(4-methyl-5-isoxazolyl)phenol.

16. A method according to claim 11 which is 2-(4-methyl-5-isoxazolyl)phenol.

17. A method according to claim 11 which is 4-methyl-2-(4-methyl-6-isoxazolyl)phenol.

18. A method according to claim 11 which is 4-chloro-2-(4-methyl-5-isoxazolyl)phenol.

19. A method according to claim 11 which is 2,4-dichloro-6-(5-isoxazolyl)phenol.

20. A method according to claim 11 which is 4-chloro-2-(5-isoxazolyl)phenol.

21. A composition comprising a fungicidal amount of a compound of the formula:

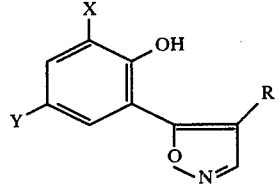

wherein X is a member selected from the group consisting of hydrogen, alkyl of from 1 to 3 carbon atoms, inclusive, chlorine or bromine; Y is a member selected from the group consisting of hydrogen, chlorine or bromine and R is a member selected from the group consisting of hydrogen or lower alkyl of from 1 to 3 carbon atoms, inclusive, in association with an inert carrier.

22. A composition according to claim 21 which is 2,4-dichloro-6-(4-methyl-5-isoxazolyl)phenol.

23. A composition according to claim 21 which is 2,4-dichloro-6-(4-ethyl-5-isoxazolyl)phenol.

24. A composition according to claim 21 which is 2,4-dibromo-6-(4-methyl-5-isoxazolyl)phenol.

25. A composition according to claim 21 which is 2-chloro-6-(4-methyl-5-isoxazolyl)phenol.

26. A composition according to claim 21 which is 2-(4-methyl-5-isoxazolyl)phenol.

27. A composition according to claim 21 which is 4-methyl-2-(4-methyl-5-isoxazolyl)phenol.

28. A composition according to claim 21 which is 4-chloro-2-(4-methyl-5-isoxazolyl)phenol.

29. A composition according to claim 21 which is 2,4-dichloro-6-(5-isoxazolyl)phenol.

30. A composition according to claim 21 which is 4-chloro-2-(5-isoxazolyl)phenol.